United States Patent [19]

Pinching et al.

[11] Patent Number: 5,122,372
[45] Date of Patent: Jun. 16, 1992

[54] PROCESS FOR TREATMENT OF ALLERGIES

[75] Inventors: Anthony J. Pinching, Middlesex; Jacqueline M. Parkin, London, both of United Kingdom

[73] Assignee: Biogen, Inc., Cambridge, Mass.

[21] Appl. No.: 47,916

[22] PCT Filed: Sep. 9, 1986

[86] PCT No.: PCT/GB86/00535

§ 371 Date: Apr. 30, 1987

§ 102(e) Date: Apr. 30, 1987

[87] PCT Pub. No.: WO87/01288

PCT Pub. Date: Mar. 12, 1987

[30] Foreign Application Priority Data

Sep. 9, 1985 [GB] United Kingdom ............. 8522336

[51] Int. Cl.$^5$ ............................................. A61K 37/66
[52] U.S. Cl. ................................... 424/85.5; 424/85.4
[58] Field of Search ............... 424/85.4, 85.5, 85.6, 424/85.7

[56] References Cited

U.S. PATENT DOCUMENTS 4,289,690 9/1981 Pesika .
4,314,935 2/1982 Uemura .
4,376,821 3/1983 Braude .
4,376,822 3/1983 Braude .
4,382,027 5/1983 Braude .
4,681,930 7/1987 Kung et al. ................... 424/85.5

FOREIGN PATENT DOCUMENTS 063482 4/1982 European Pat. Off. .
087686 2/1983 European Pat. Off. .
088540 2/1983 European Pat. Off. .
0133767 3/1985 European Pat. Off. .
0177910 4/1986 European Pat. Off. .
0181455 5/1986 European Pat. Off. .
8301198 10/1982 World Int. Prop. O. .

OTHER PUBLICATIONS

W. R. Benjamin et al., "Production of Immune Interferon by an Interleukin 2-Independent Murine T Cell Line," Proc. Natl. Acad. Sci. USA, 79, pp. 5379-5383 (1982).
M. De Lay et al., "Interferon Induced in Human Leukocytes by Mitogens: Production Partial Purification and Characterizatikn," Eur. J. Immunol., 10, pp. 877-883 (1980).
R. Derynck et al., "Expression of the Human Interferon-Gamma CDNA in Yeast," Nucleic Acids Research, 11, pp. 1819-1837 (1983).
R. Devos et al., "Isolation and Characterization of IFN-Gamma MRNA Derived from Mitogen-Induced Human Splenocytes," J. Interferon Res., 2, pp. 409-420 (1982).
R. Derynck et al., "Human Interferon Gamma is Encoded by a Single Class of MRNA", Nucleic Acids Research, 10, pp. 3605-3613 (1982).
R. Devos et al., "In Vitro Translation and Characterization of Human IFN-Gamma MRNA", J. Clin. Hematol. Oncol., 11(4), p. 114 (1981).
R. Devos et al., "Molecular Cloning of Human Immune Interferon CDNA and its Expression in Eukaryotic Cells," Nucleic Acids Research, 10(8), pp. 2487-2501 (1982).
F. Dianzani et al., "Human Immune Interferon: Induction in Lymphoid Cells by a Calcium Ionophore", Infection and Immunity, 29, pp. 561-563 (1980).
N. B. Finier et al., "Physiological and Defective Production of Interferon in Man", Interferon, 4, pp. 147-154 (1985).
G. W. Fishbein, "Schering-Plough Summarizes Recent Gains in Biotechnology," Genet. Eng. Lett., 4(12), p. 3 (1984).
Jaffe et al., "Complications of Co-Trimoxazole in Therapy of Aids-Associated Pneumocysits Carinii Pneumonia in Homosexual Men", Lancet, III, pp. 1109-1111 (1983).
H. W. Murray et al., "Impaired Production of Lymphokines and Immune (Gamma) Interferon in the Acquired Immuno-Deficiency Syndrome", N. England J. Med., 310, pp. 883-889 (1984).
Naray-Fejes-Toth et al., "Recombinant Human Immune Interferon Induces Increased IGE Receptor Expression on the Human Monocyte Cell Line U-937," J. Immunol., 133(4), pp. 1914-1919 (1984).
J. O'Malley, "Affinity Chromatography of Human Immune Interferon", Methods in Enxymology, 78, pp. 540-545 (1981).
J. K. A. Nicholson et al., "Immunoregulatory Subsets of the T Helper and T Suppressor Cell Populations in Homosexual Men with Chronic Unexplained Lymphadenopathy", J. Clin. Invest., 73, pp. 191-201 (1984).
G. H. Reem et al., "Gamma Interferon Induction in Human Thymocytes Activated by Lectins and B Cell Lines", Infection and Immunity, 37, pp. 216-221 (1982).
A. Rubinstein et al., "Acquired Immunodeficiency Syndrome with Reversed T4/T8 Ratios in Infants Born to Promiscuous Drug-Addicted Mothers", JAMA, 249, pp. 2350-2356 (1983).
G. B. Scott et al., "Acquired Immundeficiency Syndrome in Infanis", N. Engl. J. Med., 310, pp. 76-81 (1984).
P. A. Thomas et al., "Unexplained Immunodeficiency in Children. A Surveillance Report", JAMA, 252, pp. 639-644 (1984).
Y. K. Yip et al., "Partial Purification and Characterization of Human Gamma (Immune) Interferon", Proc. Natl. Acad. Sci. USA, 78, pp. 1601-1605 (1981).

Primary Examiner—Howard E. Schain
Assistant Examiner—Choon Park Koh
Attorney, Agent, or Firm—Leon R. Yankwich; James F. Haley, Jr.; Leslie A. McDonell

[57] ABSTRACT

This invention relates to the immunotherapeutic treatment of allergies. More particularly, this invention relates to a process for treating allergies by administering to a mammal a pharmaceutically effective amount of gamma interferon.

6 Claims, No Drawings

PROCESS FOR TREATMENT OF ALLERGIES

TECHNICAL FIELD OF INVENTION

This invention relates to the immunotherapeutic treatment of allergies. More particularly, this invention relates to a process for suppressing a mammal's allergic responses to allergens by means of increasing the body's level of gamma interferon. According to this invention, natural or recombinant gamma interferons are used to suppress the allergic responses in a mammal.

BACKGROUND ART

The mechanisms involved in the induction and control of the allergic response are not completely understood. The allergic response is known to be effected by antibody-mediated (immediate-type) hypersensitivity, cell-mediated (delayed-type) hypersensitivity, or both.

The antibody which is largely responsible for immediate type hypersensitivity reactions is immunoglobulin E ("IgE"). IgE antibodies bind to the membranes of mast cells in skin or to basophils, specific membrane receptors that recognize and bind the IgE molecule. The binding affinity of these classes of receptors for IgE is very high. A. Nisonoff, *Molecular Immunology*, p. 55 (1982).

After the IgE antibody is bound to the cell receptor on the mast cell or basophil, an allergen binds to two or more IgE antibodies, causing the mast cells or basophils to release numerous granules. These granules contain the mediators of immediate hypersensitivity. These mediators have extremely potent contractile effects on the smaller airways of the respiratory tract. In mice and rats, serotonin is the principal mediator. In humans, histamine is the most important mediator of immediate hypersensitivity. SRS-A (Slow Reacting Substance of Anaphylaxis) and ECF-A (Eosinophil Chemotactic Factor) are other mediators.

The symptoms of allergies include sinusitis, rhinitis, hives, headaches, post-nasal drip, coughing, sneezing, respiratory difficulties, sore throats, allergic conjunctivitis, tightness in throat and chest, and loss of voice. In extreme cases the allergic response may cause fetal anaphylactic shock. The sneezing and respiratory difficulties are brought on by contractions of smooth muscle of the respiratory tract. The other symptoms are brought on by the inflammation caused by increased vascular permeability and the attraction of leukocytes.

Examples of antibody-mediated hypersensitivity are hay fever, asthma, food allergies and hives. This type of allergy is called atopy and it is characterized by sensitivity without prior exposure to the allergen causative agent. Delayed-type hypersensitivity is mediated by T-cells. Examples of cell-mediated hypersensitivity include allergic contact dermatitis, allergies to drugs, and a number of autoimmune diseases.

Typically, allergies are treated by a variety of drugs aimed at counteracting the symptoms of an allergic reaction. However, these prior treatments are useful only on a short term basis, and often have adverse or disadvantageous and unwanted side effects. For example, antihistamines are often used to alleviate temporarily the general discomfort caused by histamine release. Such drugs, however, cause drowsiness and therefore are not recommended for use during working hours. Corticosteroids are also used to treat severe allergic reactions. However, these compounds immunosuppress the patient and thereby increase his susceptibility to infectious disease. Inhaled salbutamol (known as albuterol in the United Sates) is commonly used by asthma patients. However, like other sympathomimetic agents, salbutamol can have side reactions such as hypertension, angina, vomiting, vertigo, and insomnia.

In view of the disadvantages of such prior allergy treatments, conventional means for treating allergies remain disappointing to the patient, as well as to the clinician. Therefore, the need exists for a process which avoids these disadvantages and provides effective treatment for allergies.

DISCLOSURE OF THE INVENTION

The present invention solves the problems referred to above by providing a process for suppressing the allergic responses of a mammal by supplementing the body's level of gamma interferon. Advantageously, the process of this invention enhances the body's natural immune response to the allergen and, therefore, does not produce the variety of side effects which often accompany conventional allergy treatments.

BEST MODE OF CARRYING OUT THE INVENTION

In order that the invention herein described may be more fully understood, the following detailed description is set forth.

In the description the following terms are employed:

IFN-$\gamma$ (or gamma interferon)—Originally termed "immune interferon", IFN-$\gamma$ is a lymphokine. IFN-$\gamma$ is naturally produced in minute quantities together with other lymphokines by stimulated lymphocytes. Its molecular weight has been determined to be 20,000-25,000 (or 17,000 without carbohydrate). IFN-$\gamma$ has also been cloned and expressed in various host-vector systems. The nucleotide sequence of cloned IFN-$\gamma$ indicates that it is composed of 146 amino acids. As used in this application, "IFN-$\gamma$" includes all proteins, polypeptides, and peptides which are natural or recombinant IFN-$\gamma$s, or derivatives thereof, and which are characterized by the immunotherapeutic activity of these IFN-$\gamma$s against allergies. These include IFN-$\gamma$-like compounds from a variety of sources such as natural IFN-$\gamma$s, recombinant IFN-$\gamma$s, and synthetic or semi-synthetic IFN-$\gamma$s.

Allergy—An abnormal or altered immunologic reaction induced by an allergen in an individual who suffers from hypersensitivity to that allergen. The allergic reaction is an antibody-antigen reaction and includes anaphylaxis, atopic diseases, serum sickens and contact dermatitis.

Allergen—The immunogen or antigen which induces the allergic response.

IgE—A glycoprotein with a molecular weight of about 130,000. This immunoglobulin is responsible for immediate-type hypersensitivity reactions. When two IgE molecules are crosslinked with an allergen, mast cells and basophils release mediators such as histamines, SRS-A and ECF-A.

This invention relates to a process for treating allergies. This process comprises the steps of treating a mammal in a pharmaceutically acceptable manner with a pharmaceutically effective dose of gamma interferon ("IFN-$\gamma$").

Among the IFN-$\gamma$s useful in the processes of this invention are the IFN-$\gamma$s produced in vitro by a variety of cells in response to various interferon inducers. For example, these IFN-$\gamma$s include IFN-$\gamma$s produced in human buffy-coat leukocytes after exposure to PHA, Con A and SEA, M. DeLay et al. "Interferon Induced in Human Leukocytes By Mitogens: Production, Partial Purification and Characterization," *Eur. J. Immunol.*, 10, pp. 877-83 (1980); in human splenocytes after stimulation with SEA, R. Devos et al., "Isolation and Characterization of IGN-Gamma mRNA Derived From Mitogen-Induced Human Splenocytes," *J. Interferon Res.*, 2, pp. 409-20 (1982); by an IL-2-independent murine T cell line after stimulation by phorbol 12-myristate 13-acetate, W. R. Benjamin et al., "Production of Immune Interferon by an Interleukin 2-Independent Murine T cell line," *Proc. Natl. Acad. Sci. USA*, 79, pp. 5379-83 (1982); in lymphoid cells by using calcium ionophore A-23187, F. Dianzani et al., "Human Immune Interferon: Induction in Lymphoid Cells by a Calcium Ionophore," *Infection and Immunity*, 29, pp. 561-63 (1980); and in thymocytes, G. H. Reem et al., "Gamma Interferon Induction in Human Thymocytes Activated by Lectins and B Cell Lines," *Infection and Immunity*, 37, pp. 216-21 (1982). See also, U.S. Pat. No. 4,376,821 and U.S. Pat. No. 4,376,822 and European patent application No. 63,482.

These natural IFN-γs have been subsequently purified to some extent and partially characterized. See, for example, U.S. Pat. No. 4,289,690, U.S. Pat. No. 4,314,935 and U.S. Pat. No. 4,382,027, European patent application No. 87,686, O'Malley, "Affinity Chromatography of Human Immune Interferon," *Methods in Enzymology*, 78 pp. 540-45 (1981), and Y. K. Yip et al., "Partial Purification and Characterization of Human γ (Immune) Interferon," *Proc. Nat'l Acad. Sci. USA*, 78, pp. 1601-05 (1981).

IFN-γs useful in the processes of this invention may also be produced in large amounts using recombinant DNA technology. See, e.g., European patent application 88,540; R. Derynck et al., "Human Interferon γ Is Encoded By A Single Class Of mRNA," *Nucleic Acids Research*, 10, pp. 3605-13, (1982); R. Derynck et al., "Expression Of The Human Interferon-λ cDNA In Yeast," *Nucleic Acids Res.*, 11, pp. 1819-37 (1983); R. Devos et al., "In Vitro Translation And Characterization Of Human IFNγ mRNA," *J. Clin. Hemator. Oncol.*, 11(4) p. 114 (1981); R. Devos et al., "Molecular Cloning of Human Immune Interferon cDNA And Its Expression in Eukaryotic Cells," *Nucleic Acids Research*, 10 (8), pp. 2487-501 (1982).

Without being bound by theory, we believe that the suppression of the allergic response in antibody mediated (immediate-type) hypersensitivity by the processes of our invention is due to the direct effect of IFN-γ on the production of IgE through a general change in cellular immunity. Specifically, because hypersensitive individuals are immunodeficient in a way that deprives the body of its control mechanism for the production of IgE, the administration according to this invention of IFN-γ, which substance is normally produced by the cell-mediated immune system in healthy individuals, supplies that missing control. As a result, the IFN-γ suppresses the production of IgE, so that the allergic reaction does not occur when the body is exposed to the offending allergen. The overall result of this treatment is to establish in hypersensitive individuals, the balance present in a normal individual's immune response to antigens.

The process of this invention may be used to treat any mammal, including cats, dogs, and humans. It is particularly useful for treating allergies, including asthma, hay fever, food allergies, spontaneous anaphylaxis and other atopic diseases.

According to this invention, mammals are treated by the pharmaceutically acceptable administration of IFN-γ in a particularly effective dosage and for a period of time sufficient to suppress to some extent the allergic response.

More specifically, mammals are preferably treated with sub-cutaneous, intravenous or intramuscular injections of between 5 $\mu g/M^2$ and 500 $\mu g/M^2$. Suppression of symptoms has been observed at doses as low as 5 $\mu g/M^2$, although lower doses may also be effective. Furthermore, higher doses also result in suppression of allergic symptoms. However, such higher doses are less preferred in treating allergies only because of their flu-like side effects. Such higher doses are, of course, useful when the IFN-γ is also being used to treat other conditions, e.g., AIDS or cancer, in addition to allergies. This treatment is usually repeated on a daily basis until a desired suppression of the allergic response is observed. However, other dosage regimens are also useful. When the symptoms have been alleviated to the desired level, treatment should cease. Patients may, however, require intermittent treatment on a long term basis, as their physicians deem necessary or appropriate.

The IFN-γ can be administered in any pharmaceutically acceptable form. According to one embodiment of this invention, the formulation is isotonic and includes human serum albumin and salt buffers.

In order that the invention described herein may be more fully understood, the following example is set forth. It should be understood that this example is for illustrative purposes only, and is not to be construed as limiting this invention in any manner.

EXAMPLE

In order to demonstrate the utility of the process of the present invention, we chose patients suffering from Acquired Immuno-Deficiency Syndrome ("AIDS"), whose severely compromised cellular immune system provides a good model for determination of the effect of IFN-γ on allergies.

Patients with AIDS have a depletion of the subset of T-cells involved not only in delayed type hypersensitivity but also in the induction of suppressor cell activity, J. K. A. Nicholson et al., "Immunoregulatory Subsets of the T Helper and T Suppressor Cell Populations in Homosexual Men With Chronic Unexplained Lymphadenopathy", *J. Clin. Invest.*, vol. 73, pp. 191-201 (1984), and may therefore have abnormal suppressor function. Patients with AIDS also characteristically have T4lymphocyte depletion and decreased production of lymphokines including interleukin-2 and IFN-γ. H. W. Murray et al., Impaired Production of Lymphokines and Immune (Gamma) Interferon in the Acquired Immuno-deficiency Syndrome," *N. Engl. J. Med.*, 310, pp. 883-89 (1984). Antibodies that mediate atopic disease, may be raised as part of the polyclonal B-cell activation seen in AIDS patients. Additionally, AIDS patients who have a history of atopic disease, appear to have a recrudescence of atopic symptoms which often coincides in time with the onset of AIDS.

An unusually high incidence of drug reactions has also been noted in AIDS patients, especially in treatment with high dose sulphonamides, H. S. Jaffe et al., "Complications of Co-trimoxazole in Therapy of AIDS-associated Pneumocystis Carinii Pneumonia in Homosexual Men", *Lancet*, vol. III, pp. 1109-11 (1983).

Also, an increased incidence of atopic eczema has been noted in infants with AIDS. G. B. Scott et al., "Acquired Immunodeficiency Syndrome in Infants," N. Eng. J. Med., vol. 310, pp. 76-81 (1984); A. Rubinstein et al., "Acquired Immunodeficiency Syndrome With Reversed T4/T8 Ratios in Infants Born to Promiscuous and Drug-addicted Mothers," JAMA, vol. 249, pp. 2350-56 (1983); P. A. Thomas et al., "Unexplained Immunodeficiency in children. A Surveillance Report", JAMA, vol. 252, pp. 639-44 (1984). Accordingly, AIDS patients are useful models for the use of IFN-γ as a treatment against allergies.

The following data demonstrate the effectiveness of IFN-γ, in this case recombinant human IFN-γ, in the immunotherapeutic treatment of allergies. The patients studied were suffering from AIDS and had developed a recrudescence of atopic disease which coincided with, or developed just before, the onset of AIDS.*

* Six AIDS patients had a recrudescence of atopic disease were studied. Two of these patients are discussed in detail, infra. Only one of the remaining four atopic AIDS patients received IFN-γ, but the seasonal nature of his atopic symptoms did not permit evaluation of a response. The three others did not receive IFN-γ. Four of the six patients developed a different atopic disorder from that suffered previously, while two experienced a recurrence of their original symptoms.

The two patients whose data are reported below, had a prior history of atopic disease but in one, the atopic feature was new to the patient. After receiving recombinant human IFN-γ in a trial of immuno-restoration both showed a striking improvement in atopic symptoms during therapy and relapsed on its cessation.

The patients were treated at St. Mary's Hospital Medical School, Department of Immunology, Wright-Heming Institute, Paddington, London. Recombinant human IFN-γ was supplied by Biogen S. A., Geneva, for clinical testing. The specific activity of Biogen's recombinant human IFN-γ was in the range of $10-20 \times 10^6$ U/mg of protein.

Table 1 summarizes data for the two patients who were evaluated after treatment with IFN-γ:

TABLE 1

ATOPIC HISTORY IN SELECTED PATIENTS

| Patient N° | Age/sex | Diagnosis | Atopic symptom | Age of onset of atopic symptoms | Relation of Atopy to onset of AIDS |
|---|---|---|---|---|---|
| A2 | 49/F | PCP | hay fever* | 16-20 yr | none |
|  |  |  | asthma | 45-49 yr | ** |
|  |  |  | milk*** | 49 yr | +1 month |
| A5 | 36/M | KS | asthma | 5-18 yr | none |
|  |  |  | asthma | 36 yr | +3 months |
|  |  |  | hay fever* | 5-10 yr | none |

PCP = Pneumocystis carinii pneumonia
KS = Kaposi's Sarcoma
* = Rhinitis, sneezing, conjunctivitis on exposure.
** = The incubation period of the HTLV III in this patient was thought to be at least 5 years, therefore it is possible that the onset of asthma was related.
*** = Swelling on tongue and lips 5-10 minutes after every exposure to undiluted milk.

As shown in Table 1, the patients had a history of atopic disease in childhood or early adult life. In the cases studied, the onset of a new atopic symptom or the exacerbation of an old one occurred either during the period of persistent generalized lymphadenopathy (PGL) which occurred with the onset of AIDS, or around the time that the patient developed overt symptoms of AIDS. In all the instances where atopy emerged during PGL, the lymphadenopathy was complicated by either fever, night sweats, weight loss, or oral candidiasis, which are thought to be prodomal symptoms for AIDS, and probably represent more subtle forms of immunodeficiency.

The two patients demonstrated substantial suppression of their allergic symptoms while receiving recombinant human IFN-γ as part of a course of therapeutic treatment aimed at immunorestoration. These patients were given IFN-γ as twice weekly intravenous infusions of 3,000 micrograms/M$^2$ (patient A2) and 10 micrograms/M$^2$ (patent A5). Patient A2 had a decrease in her marked sensitivity to milk and was able to tolerate undiluted milk without significant allergic symptoms by the end of 8 weeks IFN-γ therapy. Her asthma had been quiescent before therapy and did not recur during treatment and it was therefore not possible to monitor any response.

Prior to IFN-γ treatment, patient A5 had suffered major asthmatic symptoms necessitating the use of inhaled salbutamol at least once daily. There was no evidence of opportunistic lung infections. However, during the first 4 weeks of IFN-γ treatment his asthmatic symptoms gradually resolved; for the rest of the 8-week course and for 3 weeks following, he remained asymptomatic and did not require bronchodilator therapy. In the 4th week after cessation of IFN-γ treatment his asthma returned, though not as severely; reintroduction of IFN-γ therapy again caused resolution of the symptoms, this time within one week.

To analyze the effect of IFN-γ on the allergic response to other allergies, prick tests were also performed on each patient using 16 common allergens (Pharmacia) and a positive and negative control (histamine and diluent respectively). The tests were read at 10 minutes and were considered positive if a wheal of 2 mm or more was produced in the presence of a negative response to the control. Delayed type hypersensitivity was tested using candida albicans, purified protein derivative, and streptokinase/streptodornase injected intradermally. A positive reaction was defined as induration and erythema at the site when read at 48 hours. Serum IgE levels were also measured using a paper radio immuno-sorbant test (PRIST, Pharmacia). Finally, phenotypic lymphocyte subsets were determined by indirect fluorescent labelling with monoclonal antibodies to the T4 and T8 antigens (OKT4, OKT8, GA-FITC, Coulter) and lymphokine production was measured in the supernatants of mitogen stimulated lymphocytes.

The two patients showed increased Type 1 hypersensitivity as judged by frequent positive cutaneous prick tests with common allergens. Both these patients, however, demonstrated concomitant evidence of improvement in immune reactivity during IFN-γ therapy (Table II) manifested by conversion of previously negative delayed type hypersensitivity tests to positive.

TABLE II

|  | Patient A2 | | Patient A5 | |
|---|---|---|---|---|
|  | Pre Treatment | Post Treatment | Pre Treatment | Post Treatment |
|  | Allergic symptoms | | | |
|  | swelling lips, tongue, throat on drinking milk | able to tolerate milk without severe symptoms | asthma required daily salbutamol to control symptoms | asymptomatic, no bronchodilator |
| Kaposi's Sarcoma | — | — | 6 lesions | 1 lesion |
| DTH | 0/3 +ve | 1/3 +ve | 0/3 +ve | 1/3 +ve |
| T4 lymphs × | 0.26 | 0.48 | 0.48 | 0.77 |

TABLE II-continued

| | Patient A2 | | Patient A5 | |
| --- | --- | --- | --- | --- |
| | Pre Treatment | Post Treatment | Pre Treatment | Post Treatment |
| | Allergic symptoms | | | |
| | swelling lips, tongue, throat on drinking milk | able to tolerate milk without severe symptoms | asthma required daily salbutamol to control symptoms | asymptomatic, no bronchodilator |
| $10^x$/L IFN-gamma production by lymphocytes (mg protein) | | | | |
| unstimulated | 0 | 516 | 0 | 845 |
| + Con A | 0 | 591 | 164 | 703 |
| + PWM | 0 | 463 | 261 | 279 |
| + PHA | ND | ND | 0 | 389 |

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A process for treating allergies comprising the step of administering to a mammal a pharmaceutically acceptable composition comprising a pharmaceutically effective amount of IFN-γ.

2. The process according to claim 1, wherein the mammal is a human.

3. The process according to claim 1, wherein the IFN-γ is selected from the group consisting of natural IFN-γ, recombinant IFN-γ, and derivatives thereof which are characterized by the immunotherapeutic activity of IFN-γ against allergies.

4. The process according to claim 3, wherein the composition is administered at a dosage of from about 5 $\mu g/M^2$ to about 500 $\mu g/M^2$.

5. The process according to claim 4, wherein the dosage is 10 $\mu g/M^2$.

6. The process according to claim 1, wherein the allergy is selected from the group consisting of asthma, spontaneous anaphylaxis, hay fever, and food allergies.

* * * * *